(12) United States Patent
Clauss

(10) Patent No.: US 11,576,767 B2
(45) Date of Patent: Feb. 14, 2023

(54) DEVICE AND METHOD FOR MEASURING A MOVEMENT OF A MANDIBLE

(71) Applicant: IGNIDENT GmbH, Ludwigshafen am Rhein (DE)

(72) Inventor: Petra Ina Clauss, Rottach-Egern (DE)

(73) Assignee: IGNIDENT GmbH, Ludwigshafen am Rhein (DE)

(*) Notice: Subject to any disclaimer, the term of this patent is extended or adjusted under 35 U.S.C. 154(b) by 479 days.

(21) Appl. No.: 16/477,444

(22) PCT Filed: Jan. 12, 2018

(86) PCT No.: PCT/EP2018/050769
§ 371 (c)(1),
(2) Date: Nov. 12, 2019

(87) PCT Pub. No.: WO2018/130656
PCT Pub. Date: Jul. 19, 2018

(65) Prior Publication Data
US 2020/0060796 A1    Feb. 27, 2020

(30) Foreign Application Priority Data

Jan. 13, 2017  (DE) .......................... 102017200515.7
Sep. 19, 2017  (DE) .......................... 102017216613.4

(51) Int. Cl.
*A61C 19/045* (2006.01)
*A61B 5/11* (2006.01)
(Continued)

(52) U.S. Cl.
CPC .......... *A61C 19/045* (2013.01); *A61B 5/1114* (2013.01); *A61C 11/003* (2013.01);
(Continued)

(58) Field of Classification Search
CPC ....... A61C 19/045; A61C 19/04; A61C 19/05; A61C 19/052; G01B 7/003; A61B 5/1114
See application file for complete search history.

(56) References Cited

U.S. PATENT DOCUMENTS 8,337,202 B2   12/2012  Bando et al.
2007/0252586 A1* 11/2007 Arai ..................... A61B 5/68
                                                         324/207.13
(Continued)

FOREIGN PATENT DOCUMENTS

DE      19908844      6/2001
DE      10218435      11/2003
(Continued)

OTHER PUBLICATIONS

DE Search Report in German Appln. No. 102017216613.4, dated Apr. 9, 2018, 25 pages (with English Translation).
(Continued)

*Primary Examiner* — Heidi M Eide
(74) *Attorney, Agent, or Firm* — Fish & Richardson P.C.

(57) ABSTRACT

The disclosure relates to a system for recording, transferring and simulating a relative position and/or movement of a mandible relative to a maxilla, comprising: a transmitter coil for transmitting a magnetic measurement field; at least one sensor placed on the mandible and arranged in at least one holding device having a position marking for the sensor; a sensor positioning device provided for setting the axis-orbital plane and condylar points and comprising at least one sensor for capturing and emitting positional data; a data set of a relative movement of a mandible relative to a maxilla, the data set is generated from the sensor signals of the at least one sensor arranged on the mandible and from the positional data from the sensor signals from the sensor positioning device; and a computer for recording, processing and displaying the movement data from the data set from the sensors.

9 Claims, 7 Drawing Sheets

(51) Int. Cl.
*A61C 11/00* (2006.01)
*A61C 11/06* (2006.01)
*A61C 9/00* (2006.01)

(52) U.S. Cl.
CPC ............ *A61C 11/006* (2013.01); *A61C 11/06* (2013.01); *A61C 9/0006* (2013.01); *A61C 9/0053* (2013.01)

(56) References Cited

U.S. PATENT DOCUMENTS

| | | | | |
|---|---|---|---|---|
| 2011/0053110 | A1* | 3/2011 | Bando | A61C 9/0046 433/68 |
| 2015/0289806 | A1* | 10/2015 | Hoke | A61C 19/045 433/180 |

FOREIGN PATENT DOCUMENTS

| | | |
|---|---|---|
| DE | 112005000700 | 3/2007 |
| DE | 102007014088 | 9/2008 |
| DE | 102013004102 | 11/2013 |
| EP | 0242522 | 5/1991 |
| JP | 2989600 | 12/1999 |
| WO | 2009149678 | 12/2009 |
| WO | 2018130656 | 7/2018 |

OTHER PUBLICATIONS

PCT International Search Report and Written Opinion in International Appln. No. PCT/EP2018/050769, dated Jun. 8, 2018, 11 pages (with English Translation).

PCT International Search Report on Patentability in International Appln. No. PCT/EP2018/050769, dated Jul. 16, 2019, 9 pages (With English Translation).

* cited by examiner

DEVICE AND METHOD FOR MEASURING A MOVEMENT OF A MANDIBLE

CROSS REFERENCE TO RELATED APPLICATIONS

This application is a U.S. National Phase Application under 35 U.S.C. § 371 of International Application No. PCT/EP2018/050769, filed on Jan. 12, 2018, which is claims the benefit of Application No. DE 10 2017 216 613.4, filed on Sep. 19, 2017, and Application No. DE 10 2017 200 515.7, filed on Jan. 13, 2017, the entire contents of each of which are hereby incorporated by reference.

The invention relates to a system for transferring and simulating a relative position and/or relative movement, measured at a patient, of a mandible (UK) relative to a maxilla (OK) of the patient.

The system comprises a transmitter coil for emitting a magnetic measurement field, at least one sensor attached at the mandible (UK) of the patient, said sensor being disposed in at least one holding device with a position marker for the sensor, and a suitable sensor positioning device. A data record is generated from the sensor signals of the at least one sensor disposed on the mandible (UK) of the patient and from the position data in the sensor signals of the sensor positioning device. A computer is used to implement recording, processing and presenting of the movement data from the data record of the sensor(s), wherein three-dimensional imaging of the motion sequence without articulator is implemented by fusing the position data and movement data, and wherein therapeutic positions are also able to be set without an articulator.

Alternatively or additionally, the system has an analog articulator, a real, three-dimensional model from an impression of the maxilla (OK) and/or the mandible (UK) for introduction in the analog articulator, and a suitable sensor positioning device. A data record is generated from the sensor signals and the position data in the sensor signals of the sensor positioning device. A computer is used to implement, in a virtual articulator, the recording, processing and presenting of the position data and/or movement data from the sensors, wherein therapeutic positions are able to be set.

The invention also relates to a corresponding method, with or without articulator, for simulating movement using the proposed systems.

Digital or physical impressions of the mandible and the maxilla of a patient are required for very different purposes in dentistry. A conventional type of physical impression lies in, for example, the use of an impression device, more particularly an impression tray, where an impression of the maxillary teeth including soft tissue or the mandibular teeth including soft tissue is pressed into an impression compound. Digital prints of the teeth of the maxilla and the mandible can also be captured by means of an intraoral scanner and digital image processing.

However, both ways of producing the impressions of maxilla or mandible are restricted in that neither an articulation, in particular the central occlusion, nor the movement of the mandible toward the maxilla can be imaged. However, this movement of the mandible toward the maxilla also needs to be taken into account, for example when manufacturing dentures. For this reason, the relationships between mandible, maxilla and the mandibular joint are often measured by way of auxiliary means, such as, e.g., face-bows, etc., and transferred to digital (virtual) or real (analog) articulators. However, these methods are comparatively inaccurate on account of the indirect measurement of the movement. Consequently, the movement can only be simulated following assumptions.

Document DE 102 18 435 A1 presents a method and an apparatus for a three-dimensional movement analysis of tooth surfaces of the maxilla with respect to the mandible. The apparatus comprises a maxilla sensor, which is disposed on a face-bow and which records the movement of a bite plate that is securely connected to the maxilla. Further, the apparatus comprises a mandible sensor that is mechanically rigidly connected to the mandible by way of an aid. A position, and hence also a movement, of the mandible relative to the maxilla can be recorded by evaluating the signals of the maxilla sensor and the mandible sensor by way of a referencing of the sensors relative to the maxilla and to the mandible.

Document DE 11 2005 000 700 T5 discloses an apparatus for measuring a position of a mandible relative to a maxilla, wherein magnetic field sensors and magnetic field generators are disposed in the mouth of the patient in order to determine the positions.

Consequently, the invention is based on the object of providing a system and a method for transferring and simulating a relative position and/or relative movement, measured at a patient, of a mandible (UK) relative to a maxilla (OK) of the patient, which system and method are distinguished by high measurement accuracy for presenting and simulating short movements and mastication movements and which facilitate therapeutic functional settings, which take account of such a short movement.

This object is achieved by a system as described herein, and by a method as described herein. Preferred or advantageous embodiments of the invention emerge from the dependent claims, the following description and the attached figures.

The subject matter of the invention relates to a system that is suited and/or embodied to transfer and precisely simulate a relative position and/or relative movement, measured at a patient, of a mandible (UK) relative to a maxilla (OK) of the patient.

To this end, the system comprises a transmitter coil for emitting a magnetic measurement field, wherein a transmitter coil is disposable in extraoral fashion to the side or above the maxilla (OK) in a position fixed in place with respect to the maxilla and at least one sensor attached to the mandible (UK) of the patient, said sensor being disposed in at least one holding device with a position marker for the sensor.

Furthermore, the system comprises a sensor positioning device for setting a reference plane on the skull of the patient, preferably the axis-orbital plane, comprising at least one second sensor for receiving and transmitting position data, wherein the sensor positioning device, at least with the tip thereof, is introducible into the position marker of the holding device. A substantial advantage of this digitally operating system consists of no articulator, be it manual or virtual, being required on account of the set condyle positions and the infraorbital point as a reference plane; instead, all movements are calculated with respect to the condyle points and dentures can consequently be produced directly.

Camper's plane or the Frankfurt horizontal, or any other retrievable plane on the skull, can be chosen as further additional reference planes.

Furthermore, the system comprises a data record of a relative movement, measured at a patient, of a mandible (UK) relative to a maxilla (OK) of the patient, wherein the data record is generated from the sensor signals of the at least one sensor disposed on the mandible (UK) of the patient and from the position data in the sensor signals of the sensor positioning device with respect to the aforementioned reference plane, and a computer for recording, processing and presenting the movement data from the data record of the sensor(s), wherein three-dimensional imaging of the motion sequence is implemented by fusing the position data and movement data, and therapeutic and/or function-relevant positions or functions are able to be set.

Preferably, the sensor positioning device is embodied with at least one sensor as a sensor stylus and is freely movable.

By preference, the sensor positioning device, with at least one sensor, at least with the tip thereof, is introducible into the position marker of the holding device in order to define and/or calibrate the sensor zero with its tip.

Preferably, the sensor positioning device with the at least one sensor defines the reference plane, for example the axis-orbital plane, by way of at least three measurement points.

Further preferably, the sensor positioning device with at least one sensor defines the condyle spacing by way of at least two condyle measurement points, the computer ascertaining the condyle middle.

Preferably, the position marker in the holding devices is embodied as a conical cutout, the tip of which defines a zero of the relationship of the sensor tip with respect to the relative position and/or relative movement of the mandible (UK) relative to the maxilla (OK).

Preferably the tip of the position marker has a direct relationship with a planar surface region around a cutout of the holding device, wherein the sensor position is defined with respect to the relative position and/or relative movement of the mandible (UK) relative to the maxilla (OK).

Preferably, the position marker is embodied to receive at least the tip of the sensor positioning device in interlocking fashion.

The method according to the invention for transferring and simulating a relative position and/or relative movement, measured at a patient, of a mandible (UK) relative to a maxilla (OK) of the patient using the above-described system includes the following steps of:
  disposing at least one sensor at at least the mandible (UK) of the patient, wherein the sensor is disposed in at least one holding device with a position marker for the sensor;
  setting the reference plane by way of 3 measurement points including the condyle points by means of the sensor positioning device, wherein the reference plane for the software is defined by scanning the condyle points to the right and left and by scanning the infraorbital point. A substantial advantage of this digitally operating method consists of no articulator, be it manual or virtual, being required on account of the set condyle positions and the infraorbital point as a reference plane; instead, all movements are calculated with respect to the condyle points and dentures can consequently be produced directly.
  introducing at least the tip of the sensor positioning device into the position marker, embodied as a conical cutout, in the holding devices for setting the zero of the relationship of the sensor tip with respect to the relative position and/or relative movement of the mandible (UK) relative to the maxilla (OK);
  recording and processing sensor signals of the sensor;
  generating a data record from the sensor signals of the at least one sensor disposed on the mandible (UK) of the patient and from the position data in the sensor signals of the sensor positioning device;
  processing and presenting the movement data from the data record of the sensor(s), wherein three-dimensional imaging of the motion sequence is implemented by fusing the position data and movement data, and therapeutic positions or functions are able to be set.

A particular advantage of the method consists of the software placing the holding device as a data record over the scanned, cast sensor shoe and subsequently, virtually in the software, clicking the sensor center, e.g., by means of a PC mouse, and thus determining the start position of the recorded movements anew.

This means that the sensor shoes are retrieved in the software, are superposed with the original data record of the sensor shoe in order then, following the alignment of the models, to determine the sensor center in turn, once again by clicking, e.g. using a PC mouse, sensor positioning device, in order to define the start position of the recorded movements.

The alternative or complementary system comprises an analog articulator, a real, three-dimensional model from an impression of the maxilla (OK) and/or the mandible (UK) for introduction into the analog articulator, and a virtual articulator for receiving, processing and presenting the position data and/or movement data from sensors, wherein therapeutic positions or functions are able to be set. If a plurality of relative positions are recorded in a temporal sequence, the system serves to determine and simulate a relative movement of the mandible relative to the maxilla in all three movement directions in the joint space of the patient.

To this end, the system comprises a real, three-dimensional model of an impression of the maxilla (OK) and/or the mandible (UK) for introduction into the analog articulator, wherein holding devices with position markers for sensors are modeled into the model, and a sensor positioning device comprising a plurality of sensors for receiving and transmitting position data and/or movement data, said sensor positioning device being able to be placed on the real, three-dimensional model. Further, the system comprises a virtual articulator for receiving, processing and presenting the position data and/or movement data from the sensors, wherein three-dimensional imaging of the motion sequence is implemented by fusing the three-dimensional model from the position markers with the determined relative position and/or relative movement and therapeutic positions are able to be set.

From a measuring point of view, the mandible is the important jaw as it moves. The mandible sensor consequently records the relative movement. The maxilla sensor preferably forms a reference sensor for the mandible sensor. The maxilla sensor can moreover eliminate a head movement by way of calculation by means of a computer program. This is also conceivable without a sensor, and so the mandible sensor can record a relative movement even without a reference sensor in the maxilla.

The mandible sensor and the maxilla sensor—also referred to as sensors below in summarizing fashion—are embodied as position sensors, for determining a position, more particularly an absolute position, in a measurement field in each case. In particular, the sensors are embodied to determine at least three translational degrees of freedom. Since the sensors are securely connected to the mandibular model or the maxillary model and the positions can be detected, the location and orientation, more particularly the relative location and orientation and/or relative movement, between the maxilla and mandible is easily determinable from the available data. Preferably, the position of the sensors is determined such that these are referenceable by way of an additional sensor device.

An advantage here is that the movements which were recorded at the patient are very precisely virtually replicable and therapeutic functional settings are facilitated. The positions are recorded directly where these are most accurate, specifically at the teeth of the mandible or the maxilla or—should these not be present—by way of aids that are likewise disposed in the vicinity. The measuring technique by way of the sensors embodied as magnetic field sensors, in particular, has become well-established in the meantime, and so large measurement inaccuracies are not to be expected here either.

Consequently, the system represents a measurement system and a simulation system, by means of which the relative movement of mandible with respect to maxilla can be recorded very accurately with high accuracy and a low structural outlay, can be presented in analog and virtual fashion and can be used for setting therapeutic functions, for example when producing a dental splint. An essential difference from known articulators consists in the fact that, inter alia, the intercondylar distance measured at the patient is set first, in particular in order to be able to precisely image movements to the right and left, i.e., short movements and grinding movements of the jaw, both in the analog and virtual articulator and/or movement simulator.

In order to be able to set the real, three-dimensional models, preferably made of plaster, in the analog articulator, the system preferably comprises a sensor positioning device embodied as an elastic metal brace, on which at least one, preferably three sensors are disposed. The sensors advantageously engage in the plaster holding devices with position markers for sensors, disposed on the plaster model, in interlocking fashion.

By preference, the sensor(s) is/are displaceably disposable on the sensor positioning device in order to be adapted continuously to the respective model geometry and the location and orientation of the position markers.

By preference, the sensor(s) is/are embodied as sensor tip(s), which is/are disposable on the real, three-dimensional model of the maxilla (OK) and/or the mandible (UK) in force-fit fashion, for example by means of setscrews.

By preference, the sensors are calibrated to the respective sensor tip and the respective tip defines a zero of the relationship of the sensor with respect to the relative position and/or relative movement of the mandible (UK) relative to the maxilla (OK), i.e., a horizontal plane.

By preference, the position of the respective sensor tip is defined with respect to the relative position and/or relative movement of the mandible (UK) relative to the maxilla (OK).

In respect of the position markers in the plaster holding devices of the real, three-dimensional plaster model, these are preferably embodied as a conical cutout, the tip of which defines a zero of the relationship of the attached sensor tip with respect to the relative position and/or relative movement of the mandible (UK) relative to the maxilla (OK).

Preferably, the tip of the position marker has a direct relationship with a planar surface region around the cutout of the holding device, wherein the sensor position is defined with respect to the relative position and/or relative movement of the mandible (UK) relative to the maxilla (OK).

By preference, the position marker is embodied to receive the sensors in interlocking fashion.

Both the analog articulator and the virtual articulator are preferably adjustable with the measured position data and/or movement data.

The measured intercondylar distance is able to be set in the analog articulator and the virtual articulator.

A plurality of complicated individual motion sequences, such as opening, closing, masticating, and short movements to the right and left, such as grinding, are able to be simulated both in the analog and in the virtual articulator.

The alternative method according to the invention for transferring and simulating a relative position and/or relative movement, measured at a patient, of a mandible (UK) relative to a maxilla (OK) of the patient using the above-described system includes the following steps:

creating the real, three-dimensional plaster model from an impression of the maxilla (OK) and/or the mandible (UK), wherein holding devices with position markers for sensors are modeled into the model;

introducing the real, three-dimensional model of the maxilla (OK) and/or the mandible (UK) into the analog articulator;

applying the sensor positioning device with at least one, preferably three sensors for receiving and transmitting position data and/or movement data on the real, three-dimensional model;

disposing the sensors of the sensor positioning device in the position markers at the maxilla (OK) and at the mandible (UK) of the real, three-dimensional model;

recording sensor signals of the sensors;

determining a relative position and/or relative movement between the maxilla (OK) and the mandible (UK) on the basis of the sensor signals;

setting the measured intercondylar distance;

receiving and transmitting position data and/or movement data;

creating a digital, three-dimensional model of the maxilla (OK) and/or the mandible (UK), and fusing the three-dimensional model with the determined relative position and/or relative movement for the purposes of producing an imaging of the motion sequence;

imaging the motion sequence and setting therapeutic positions and/or functions in the analog and/or virtual articulator.

Further, the method comprises the transfer of the motion sequence into a computer program as a virtual actuator, wherein, virtually, a plurality of complex individual motion sequences, such as opening, closing, masticating, and short movements to the right and left, such as grinding, are able to be simulated.

A particular advantage of this method, too, consists of the software placing the holding device as a data record over the scanned, cast sensor shoe and subsequently, virtually in the software, clicking the sensor center, e.g., by means of a PC mouse, again in order to define the start position of the recorded movements.

This means that the sensor shoes are retrieved in the software, are superposed with the original, real sensor shoe in order then, following the alignment of the models, to click on the sensor center, in turn, e.g. using a PC mouse, again in order to define the start position of the recorded movements.

In a preferred configuration of the invention, the sensors are embodied moreover to determine at least two rotational degrees of freedom, preferably all three rotational degrees of freedom or six degrees of freedom (three translational degrees of freedom and three rotational degrees of freedom), in the measurement field. In particular, the sensors are embodied as five-DOF (degrees of freedom) sensors or even as six-DOF sensors. All three translational degrees of freedom and two rotational degrees of freedom can be detected in the embodiment as five-DOF sensors. All three translational degrees of freedom and all three rotational degrees of freedom can be detected in the embodiment as six-DOF sensors. Once again, the measurement is improved by the detection of the rotational degrees of freedom, and so the measurement accuracy of the system can be improved further. In one exemplary embodiment, the sensors consist of 2 5DOF sensors, which become a 6DOF sensor as a result thereof. Hence, two measurement points in the mandible and two measurement points in the maxilla, i.e., four measurement points, can be recorded in the x-, y-, and z-direction in order to determine a relative movement therefrom.

In a particularly preferred configuration of the invention, either exactly two five-DOF sensors or exactly one six-DOF sensor is selectively disposed in each case at least on the mandible of the plaster model. In particular, exactly one six-DOF sensor is disposed on the maxilla and exactly one six-DOF sensor is disposed on the mandible.

In a preferred configuration of the invention, the shortest distance between the respective sensor and the tooth model on which the sensor is disposed is preferably formed as less than 0.5 centimeters and, more particularly, less than 0.3 centimeters. What is achieved by positioning the sensors close to the teeth is that measurement errors on account of distances or continuations between the sensors and the teeth are avoided.

In a preferred configuration of the invention, the plaster model comprises one holding device per jaw, wherein the holding devices were fastened to the real mandible and/or the maxilla of the patient as holding devices for sensors. Consequently, the plaster holding devices form a mechanical connection between the teeth and the sensors. As an alternative thereto, the sensors may also be fastened to the jaw or to the teeth of the real jaw in interlocking fashion only. Particularly preferably, the respective holding devices were formed at the real maxilla (OK) and/or the mandible (UK) of the patient as a sensor shoe, which is able to be bonded to the respective teeth.

As a consequence, the plaster model likewise has the form of the sensor shoe without, however, containing a sensor.

The plaster sensor shoe has at least one curved surface region and at least one position marker.

Preferably, the position marker is embodied as an indentation or cutout in the curved surface region, facing away from the respective tooth, of the plaster sensor shoe.

Further preferably, the position marker is embodied as a conical cutout, the tip of which defines a zero of the relationship of the sensor with respect to the relative position and/or relative movement of the mandible (UK) relative to the maxilla (OK).

Here, the tip of the position marker has a direct relationship with a planar surface region around the cutout of the plaster sensor shoe, wherein the sensor position is defined with respect to the relative position and/or relative movement of the mandible (UK) relative to the maxilla (OK).

Preferably, the position marker is disposed centrally on the plaster sensor shoe.

The plaster sensor shoe comprises at least one curved surface region facing the respective tooth or teeth and said plaster sensor shoe is embodied for receiving a maxilla sensor and/or a mandible sensor in interlocking fashion.

In an alternative configuration of the invention, the system comprises a digitization device for creating a digital, three-dimensional model of the maxilla and/or the mandible, wherein the holding devices and/or the sensors are modeled into the model. By way of example, the digitization device can be embodied as an intraoral scanner. In preferred embodiments of the invention, the maxilla and the mandible of the patient are cast mechanically or physically, in particular as a plaster model, and these can subsequently be digitized in a 3D scanner. However, provision is made in both embodiments for the holding device and/or position marker to also be cast or digitized such that the relative position and orientation between the sensors or holding devices and the maxilla and the mandible are uniquely determined. As an alternative thereto, a further sensor positioning device (pointing tool) is used. Using this, the position of the sensors in the mouth can be determined and can be transferred into the digitization device. In particular, the sensor device is a sensor tip, by means of which one orientation point is recorded in each case at at least 3 retrievable points. Then, these points reference to the sensors. Corresponding software calculates the position of the adhesively bonded sensors.

In this way, it is possible during the subsequent data processing to not only determine the relative position and relative movement of the sensors with respect to one another as a movement of the mandible relative to the maxilla but also to model the contour of the teeth of the maxilla and the contour of the teeth of the mandible relative to one another.

The method comprises a step of creating a digital, three-dimensional model of the maxilla and/or the mandible, wherein the holding device and/or the position markers are modeled into the model. In a further step, the data of the sensors are fused with the model of the maxilla and the mandible, more particularly in an evaluation device, such that a model of the maxilla and the mandible is formed in various relative positions and/or in relative movement with respect to one another. In particular, the model comprises a motion sequence, wherein the motion sequence comprises a plurality of complicated individual motion sequences, such as opening, closing, masticating, grinding, etc. In this way, it is possible to determine paths of movement of the mandible relative to the maxilla.

A particular advantage of this method, too, consists of the software placing the holding device as a data record over the scanned, cast sensor shoe and subsequently, virtually in the software, determining the sensor center by means of the tip of the sensor positioning device again in order to define the start position of the movements to be recorded or recorded movements.

This means that the sensor shoes are retrieved in the software, superposed with the original, real sensor shoe in order then once again to determine the sensor center by means of the tip of the sensor positioning device again following the alignment of the models in order to define the start position of the movements to be recorded.

Further features, advantages and effects of the invention emerge from the subsequent description of a preferred exemplary embodiment of the invention and the attached figures. In detail:

Figure 1:
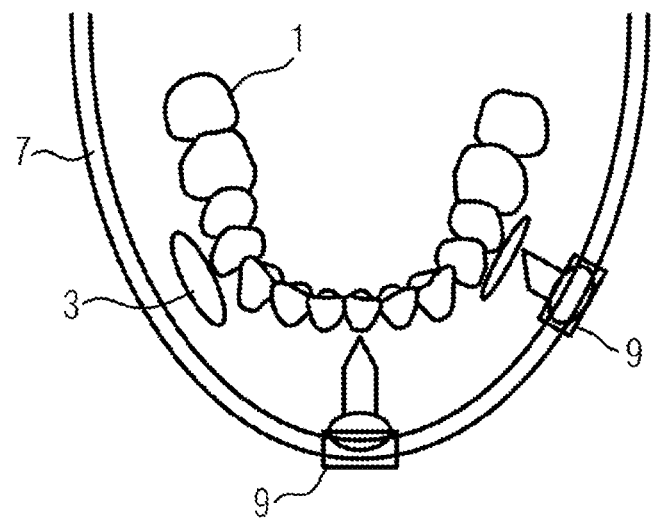
FIG. 1 shows a schematic plan view of a sensor positioning device with at least three sensors for attachment to the real, three-dimensional plaster model of maxilla or mandible.

In a very schematic illustration, FIG. 1 shows a sensor positioning device 7 according to the invention with three sensors 9 for attachment to the real, three-dimensional plaster model 1 of the maxilla or mandible. By way of example, the sensor positioning device 7 is embodied as an elastic metal brace, on which at least one, preferably three or more sensors 9 are disposed. The sensors 9 engage in interlocking fashion with the sensor tips in the plaster holding devices 3, provided on the plaster model 1, with position markers 5 for the sensors 9 disposed therein.

The position marker 5 is embodied as an indentation or cutout in the curved surface region, facing away from the respective tooth, of a holding device 3 represented as a plaster sensor shoe. In particular, the position marker 5 is embodied as a conical cutout such that the tip thereof defines a zero of the relationship of the sensor 9 with respect to the relative position and/or relative movement of the mandible (UK) relative to the maxilla (OK). The tip of the position marker 5 has a direct relationship with a planar surface region around the cutout of the sensor shoe 3, wherein the sensor position is defined with respect to the relative position and/or relative movement of the mandible (UK) relative to the maxilla (OK).

Figure 2:
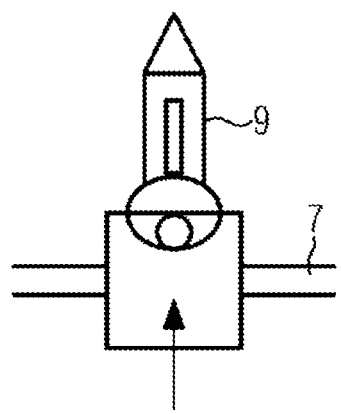
FIG. 2 shows a schematic illustration of a sensor with a sensor tip, which is displaceably disposed on the sensor positioning device.

FIG. 2 shows a schematic illustration of a sensor 9 with the sensor tip, which, for example by means of a setscrew, is disposed in lockable and displaceable fashion on the elastic metal brace 7. The sensor 9 engages into the position marker 5 with the sensor tip in interlocking fashion.

Preferably, three sensors 9 are required in order to be able to image a plane in the virtual articulator.

Figure 3:
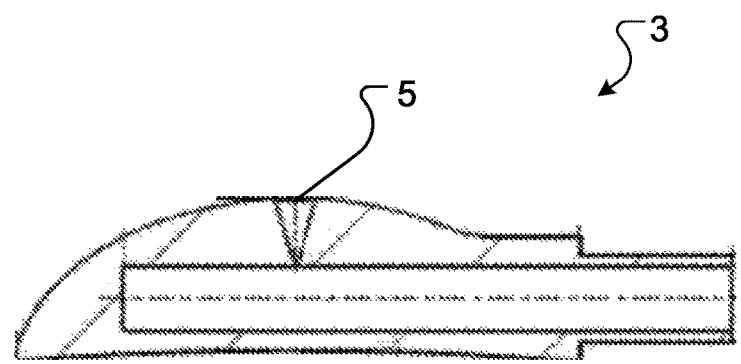
FIGS. 3-5 show a schematic side view, plan view and oblique view of a holding device, embodied as a plaster sensor shoe, with a position marker.
Figures 4A, 4B:
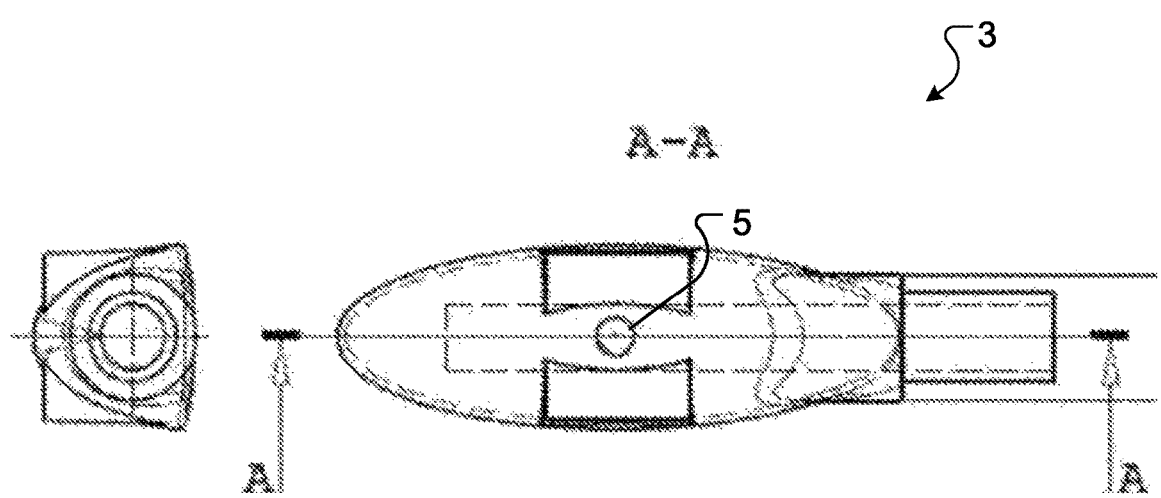
Figures 5A, 5B:
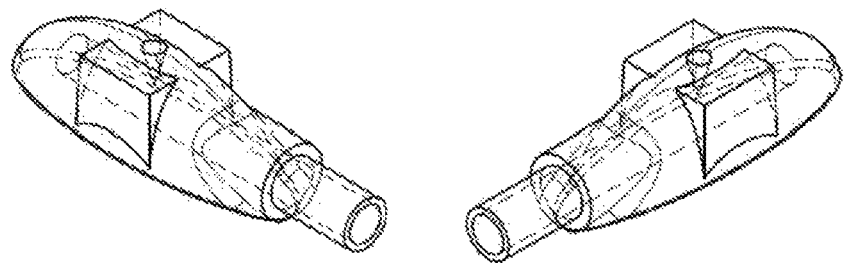

FIGS. 3-5 show a schematic side view, plan view and oblique view of an original sensor shoe, which is fastenable to the respective teeth or to a mandibular aid of the mandible (UK) or a maxillary aid of the maxilla (OK) and the plaster cast of which corresponds to the holding device 3. In its form with a slightly arched sole, the sensor shoe is chosen in such a way that it is easy to adhesively bond to the teeth and can even be used in the case of little space.

The relative position and/or relative movement is measured at a patient and the real three-dimensional model 1 such that the patient's natural jaw movements are recorded, e.g. when masticating, opening and closing, moving laterally to the left, moving laterally to the right, during protrusion and during retrusion. The sensors are connected to an evaluation device by way of a wired connection, wherein sensor signals are guided from the sensors to the evaluation device by way of the cable device. The virtual articulator is integrated in software in this case.

The sensors 9 are embodied as magnetic field sensors and allow the detection of at least one absolute position in the measurement field. Consequently, an absolute position of the sensors relative to a transmitter coil can be determined from the sensor signals. The absolute position can be output, for example, as XYZ coordinates in a coordinate system K, which is linked to the transmitter coil in stationary fashion. Optionally, the sensors can detect further degrees of freedom, more particularly rotational degrees of freedom, in addition to the absolute position, i.e. three translational degrees of freedom. In this exemplary embodiment, the sensors 9 are each embodied as a six-DOF sensor and are consequently magnetic field sensors that can record the three translational and three rotational degrees of freedom in the magnetic field as a measurement field. The sensor signals are forwarded by way of the cable device to the evaluation device, where they are processed further. By way of example, the evaluation device is embodied as a computer or as any other digital data processing device.

The evaluation device has a storage device in which a 3D model of the maxilla OK and of the mandible UK is saved. The sensors 9 are respectively included and/or modeled in the 3D model. Since the positions relative to a transmitter coil are known by way of the sensors, the 3D models of the maxilla OK or of the mandible UK can be disposed in virtual fashion with respect to one another with the correct position and orientation. Consequently, it is possible to form an overall model in which the 3D models of the mandible UK and the maxilla OK are positioned relative to one another with the correct position and orientation such that the relative position with respect to one another is determined.

Further, a relative movement of the maxilla OK and the mandible UK can be presented in the overall model. Then, the overall model can be output by way of an interface, for example in order to be able to be used further in a virtual articulator and/or in a CAD system. In particular, the apparatus allows the output of a motion sequence, wherein the motion sequence comprises a plurality of complicated individual motion sequences, such as opening, closing, masticating, in particular lateral short movements, such as grinding, and the presentation of said motion sequence, for example like a film. In this way, paths of movement of the mandible relative to the maxilla can be determined.

The 3D models of the maxilla or the mandible are alternatively provided by way of an intraoral scanner, for example, which records the maxilla OK or the mandible UK with the attached sensors. Preferably, a cast of the maxilla OK or of the mandible UK with a cast of the sensors is digitized by way of a 3D scanner in order to obtain the 3D models.

Figure 6:
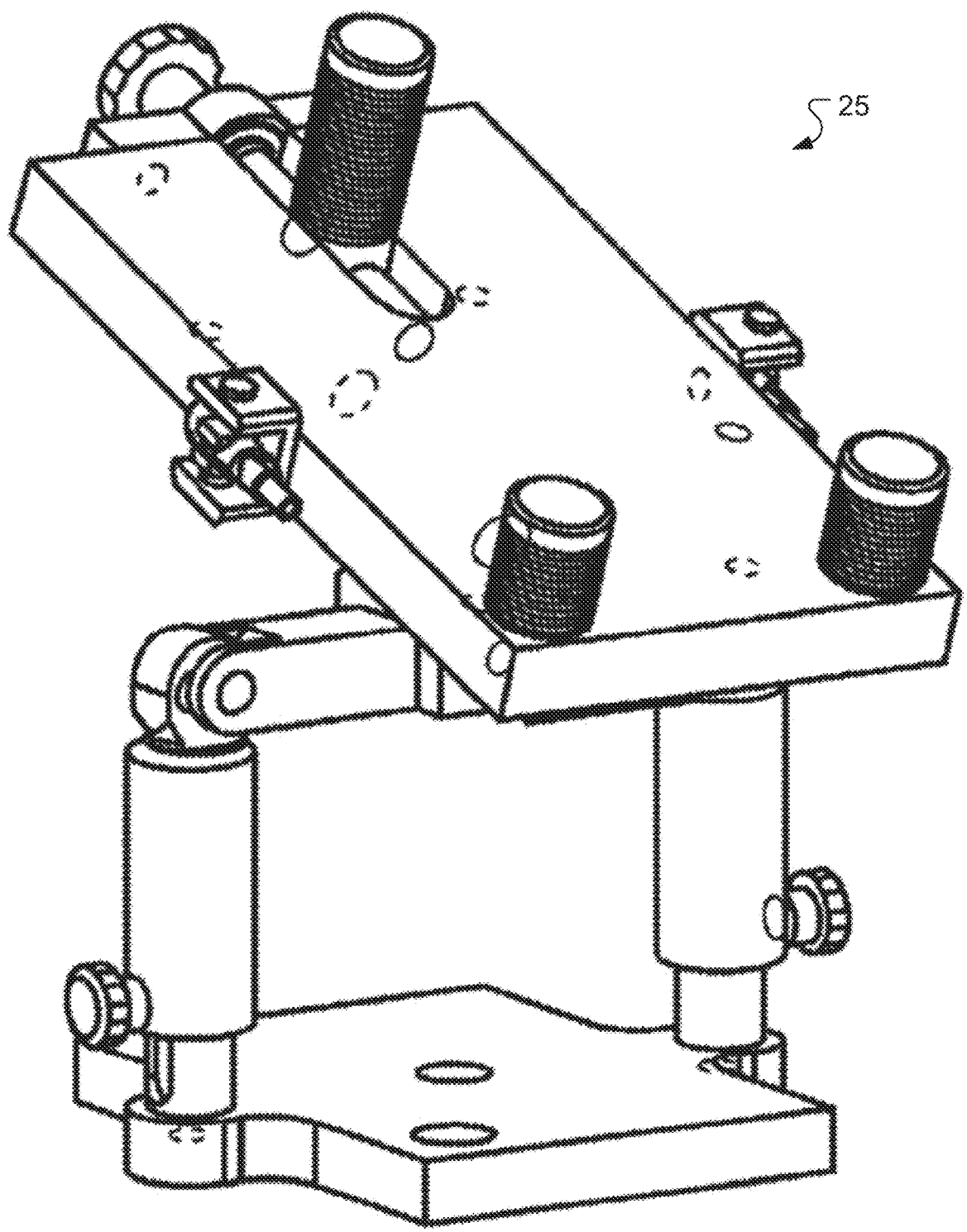
FIG. 6 shows an analog articulator.
Figure 7:
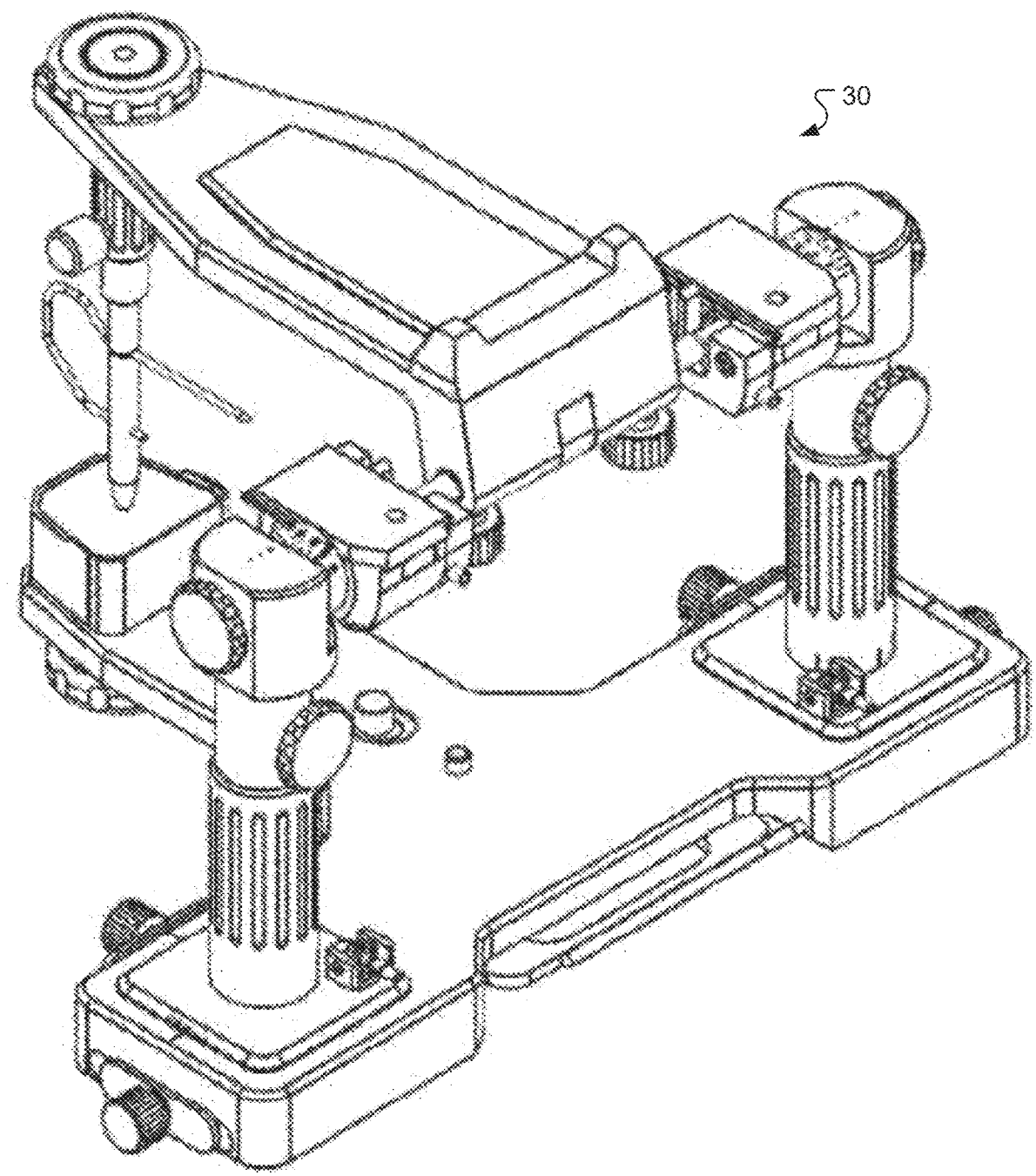
FIG. 7 shows a transfer table with movement simulator.
Figure 8:
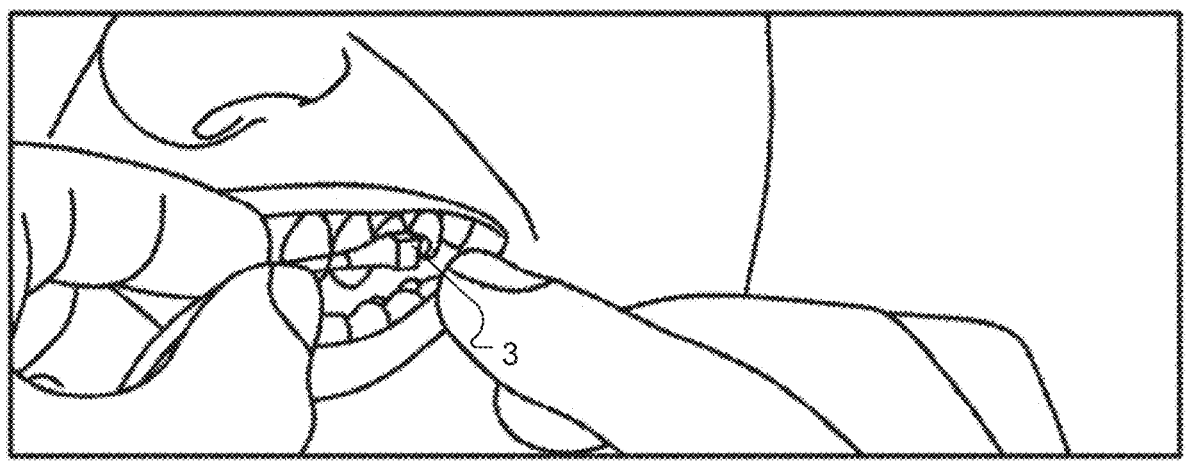
FIGS. 8-11 show a schematic view of a system according to the invention comprising a transmitter coil, at least one sensor attached to the mandible (UK) of the patient, a holding device with a position marker for the sensor, a sensor positioning device, represented as a "pointing tool", for setting the axis-orbital plane and condyle points, and a computer.
Figure 9:
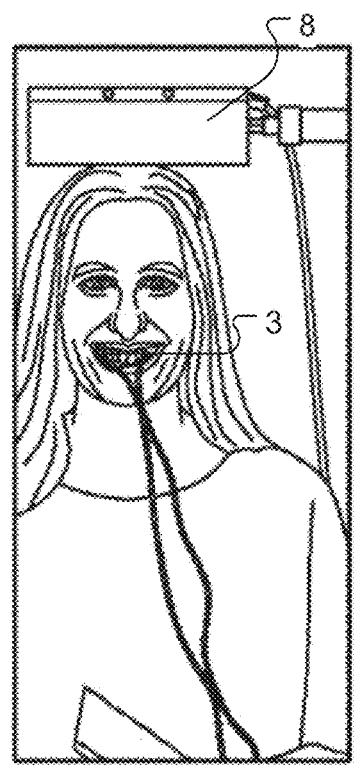

FIG. 6 shows a suitable transfer table 25 and FIG. 7 shows an analog articulator 30 as a movement simulator for transferring and simulating and a previously measured relative movement of a mandible (UK) relative to the maxilla (OK) of the patient.

The magnetic field generator 8 and the position markers 5 are used to transfer the positions in the mouth to the transfer table by means of appropriate software, wherein the magnetic field generator is positioned with respect to the worktable. By way of the software, the sensor position/position marker 5 at the transfer table is compared to the position in the mouth of the patient. By way of the software, the correct positioning of the plaster models in the transfer table is indicated by way of the holding devices 3/position markers 5 fastened there.

The articulator or movement simulator precisely simulates the movements recorded in the mouth. In order to be able to set a therapeutic position for patients or even total prosthesis wearers, markers could likewise be attached to the movement simulator, said markers then being actuated by way of software again.

Micrometer screws can be used to adjust the x-, y-, and z-axes and hence the therapeutic situation and/or function can be defined and stored in software, wherein the intercondylar distance is set as a first step since the condyles are spaced apart to a different extent in different people.

The motion sequence is completely created in the movement simulator such that paths of movement are compared with a mandible movement detection established following the tooth replacement insertion.

An irritation of the patient is completely avoided and free movements, including mastication, are possible for the first time when recording the mandible movement.

FIGS. 8-11 show a schematic view of a system according to the invention comprising the transmitter coil 8, at least one sensor 9 attached to the mandible (UK) of the patient, a holding device with a position marker 3 for the sensor 9, a second sensor positioning device 13, represented as a stylus-like "pointing tool", for setting axis-orbital plane and condyle points, and a computer.

The relative position and/or relative movement is directly measured at a patient such that their natural jaw movement is recorded, for example when masticating, opening and closing, moving laterally to the left, moving laterally to the right, during protrusion and during retrusion. The sensors are connected to an evaluation device by way of a wired connection, wherein sensor signals are guided from the sensors to the evaluation device by way of the cable device. The virtual articulator is integrated in software in this case.

The sensors 9 are embodied as magnetic field sensors and allow the detection of at least one absolute position in a measurement field. Consequently, an absolute position of the sensors relative to a transmitter coil 8 can be determined from the sensor signals. The absolute position can be output, for example, as XYZ coordinates in a coordinate system K, which is linked to the transmitter coil in stationary fashion. Optionally, the sensors can detect further degrees of freedom, more particularly rotational degrees of freedom, in addition to the absolute position, i.e. three translational degrees of freedom. In this exemplary embodiment, the sensors 9 are each embodied as a six-DOF sensor and are consequently magnetic field sensors that can record three translational and three rotational degrees of freedom in the magnetic field as a measurement field. The sensor signals are forwarded by way of the cable device to the evaluation device, where they are processed further. By way of example, the evaluation device is embodied as a computer or as any other digital data processing device.

The evaluation device has a storage device in which a virtual 3D model of the maxilla OK and of the mandible UK is saved. The sensors 9 are respectively included and/or modeled in the 3D model. Since the positions relative to a transmitter coil are known by way of the sensors, the 3D models of the maxilla OK or of the mandible UK can be disposed in virtual fashion with respect to one another with the correct position and orientation. Consequently, it is possible to form an overall model in which the 3D models of the mandible UK and the maxilla OK are positioned relative to one another with the correct position and orientation such that the relative position with respect to one another is determined.

Figure 10:
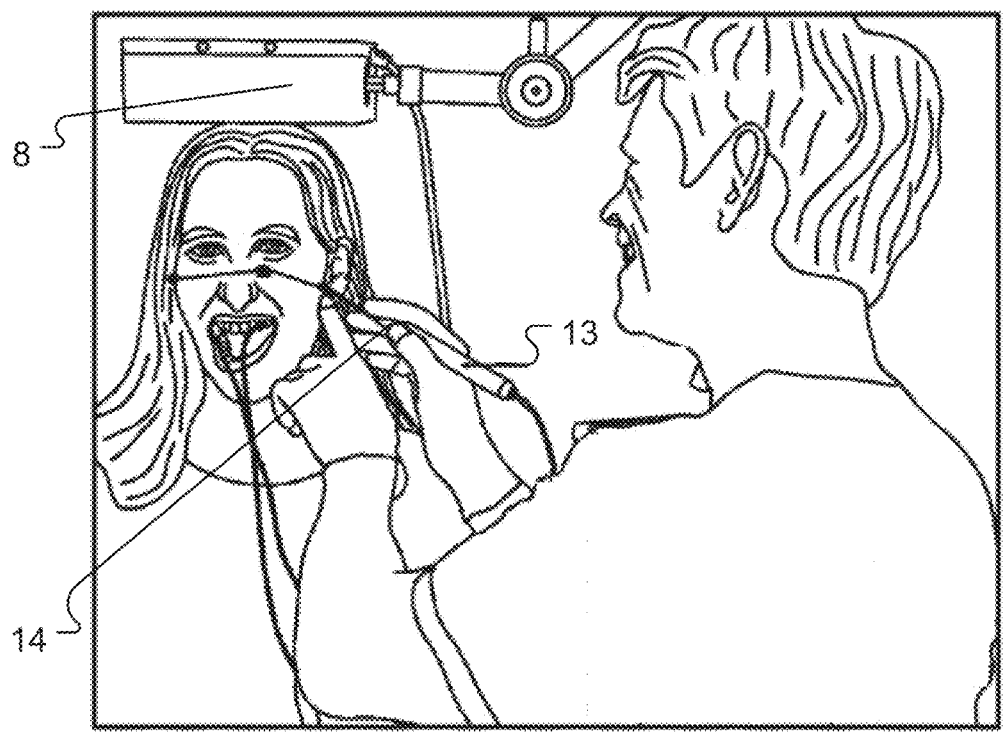
Figure 11:
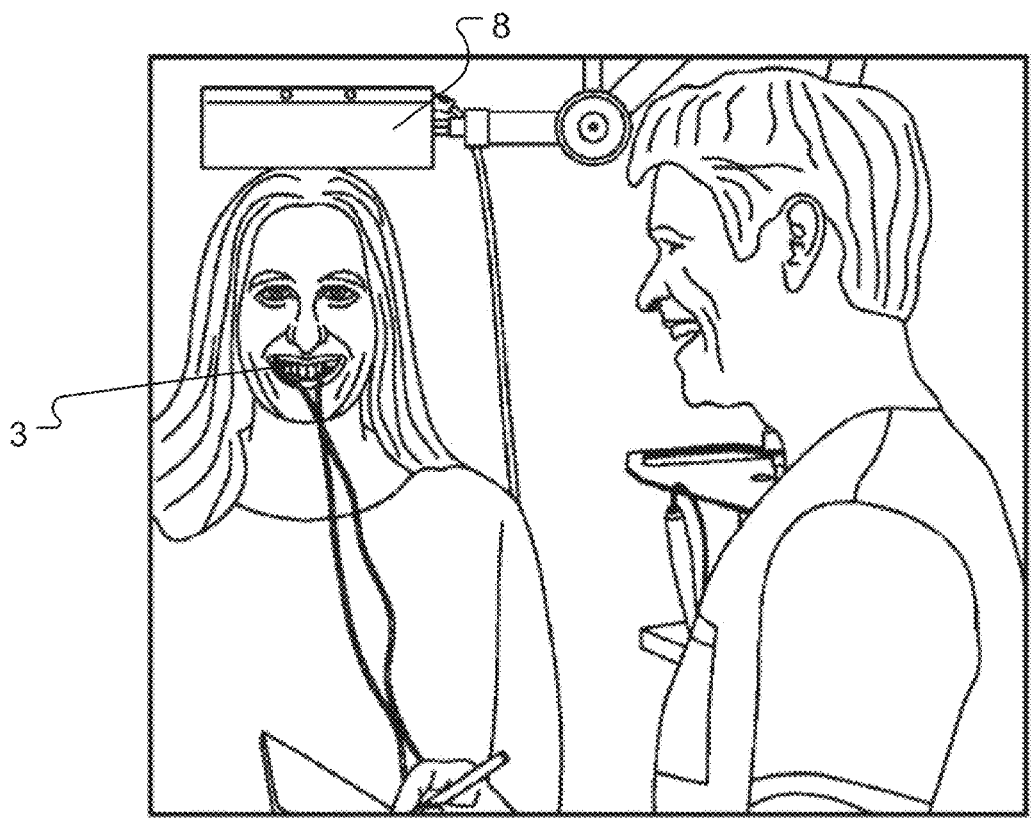

Moving the virtual 3D models, in particular the mandible in the software in relation to the maxilla in the software, requires the following guidelines:

The condyle points, cf. FIG. 10, set and probed by means of the stylus-like "pointing tool" 13 define the condylar distance. The software calculates the condyle middle independently by way of averaging.

The reference points probed by means of the "pointing tool" 13 and the reference plane set therefrom define, for example, the axis-orbital plane defined by way of 3 points or any other predetermined plane.

The introduction of the sensor positioning device 13, represented as a "pointing tool", into the position marker 5 (marker centers) embodied as a conical cutout in the holding devices 3 (marker shoe) defines the zero of the relationship of the sensor tip 14 with respect, to the relative position and/or relative movement of the mandible (UK) relative to the maxilla (OK).

Probing the marker centers 5 is implemented by means of the sensor positioning device 13 (pointing tool) is implemented after setting the condyle points and the reference plane. The marker center 5 is calibrated and/or defined at the factory as the sensor center point.

By recording the movements, which can be played back in the software, it is possible to represent any relative movement of the maxilla OK and the mandible UK in the overall model. Then, the overall model can be output by way of an interface, for example in order to be able to be used further in a virtual articulator and/or in a CAD system. In particular, the apparatus allows the output of a motion sequence, wherein the motion sequence comprises a plurality of complicated individual motion sequences, such as opening, closing, masticating, in particular short movements, such as grinding, and the presentation of said motion sequence, for example like a film. In this way, paths of movement of the mandible relative to the maxilla can be determined.

On account of the simple handling, it is likewise conceivable to combine, or attach in mobile fashion, the system according to the application to existing dental components. Thus, it is conceivable, for example, for the system according to the application to be attached or fully integrated, in addition to or as a replacement of existing imaging systems, on the treatment chair or on large appliances such as x-ray apparatuses, etc. All that would be required here is to position the device containing the transmitter coil on the treatment chair/x-ray apparatus, etc., wherein the device would also have to contain the respective interfaces or connections to the sensors and transmitter positioning devices.

The invention claimed is:

1. A system for recording, transferring and simulating a relative position and/or relative movement, measured at a patient, of a mandible relative to a maxilla of the patient, comprising:
   a transmitter coil for emitting a magnetic measurement field, wherein the transmitter coil is disposable in extraoral fashion to the side or above the maxilla in a position fixed in place with respect to the maxilla;
   at least one holding device with a position marker for at least one first sensor;
   the at least one first sensor configured to be attached to the mandible of the patient, the at least one first sensor disposed in the at least one holding device;
   a sensor positioning device for setting a reference plane relative to the transmitter coil with condyle points, the sensor positioning device comprising a sensor tip of at least one second sensor for setting the reference plane, wherein at least the sensor tip of the sensor positioning device is introducible into the position marker of the at least one holding device; and
   a computer for recording, processing and presenting relative movement from a data record of the first and second sensors generated from sensor signals of the at least one first sensor and from position data of the sensor positioning device with respect to the reference plane, wherein three-dimensional imaging of a motion sequence is implemented by fusing the position data and movement data obtained during a motion sequence of the mandible relative to the maxilla.

2. The system as claimed in claim 1, wherein the at least one second sensor comprises a sensor stylus which comprises the sensor tip, and said sensor positioning device is freely movable relative to the at least one first sensor.

3. The system as claimed in claim 1, wherein introducing said sensor positioning device into the position marker defines and/or calibrates a relationship of the sensor tip with respect to the relative position and/or relative movement of the mandible relative to the maxilla.

4. The system as claimed in claim 1, wherein the sensor positioning device with the sensor tip defines the reference plane by way of at least three points including two of the condyle points.

5. The system as claimed in claim 1, wherein the sensor positioning device with the at least one second sensor defines a condyle spacing by way of at least two of the condyle points and wherein the computer ascertains a condyle middle reference point.

6. The system as claimed in claim 1, wherein the position marker in the at least one holding device is embodied as a conical cutout, the tip of which calibrates a relationship of the sensor tip with respect to the relative position and/or relative movement of the mandible relative to the maxilla.

7. The system as claimed in claim 1, wherein the position marker comprises a cutout of the holding device, and a tip of the position marker has a direct relationship with a planar surface region around the cutout, wherein the sensor position is defined with respect to the relative position and/or relative movement of the mandible relative to the maxilla.

8. The system as claimed in claim 1, wherein the position marker is embodied to receive at least the sensor tip of the sensor positioning device in interlocking fashion.

9. A method for recording, transferring and simulating a relative position and/or relative movement, measured at a patient, of a mandible relative to a maxilla of the patient using a system as claimed in claim 1, said method comprising:
  disposing the at least one first sensor on the mandible of the patient, wherein the sensor is disposed in the at least one holding device with the position marker for the at least one second sensor;
  setting the reference plane by way of three measurement points including the condyle points by means of the sensor positioning device,
  introducing at least the sensor tip of the sensor positioning device into the position marker, embodied as a conical cutout, in the at least one holding device for calibrating the relationship of the sensor tip with respect to the relative position and/or relative movement of the mandible relative to the maxilla;
  recording and processing sensor signals from the at least one first sensor and the sensor positioning device;
  generating a data record from the sensor signals of the at least one first sensor disposed on the mandible of the patient and from the position data in the sensor signals of the sensor positioning device;
  processing and presenting relative movement data from the data record of the at least one first sensor, wherein three-dimensional imaging of the motion sequence is implemented by fusing the position data and movement data obtained during a motion sequence of the mandible relative to the maxilla.

\* \* \* \* \*